(12) United States Patent
Ross et al.

(10) Patent No.: US 7,054,409 B2
(45) Date of Patent: May 30, 2006

(54) VOLUMETRIC CT SYSTEM AND METHOD UTILIZING MULTIPLE DETECTOR PANELS

(75) Inventors: William Ross, Scotia, NY (US); Peter Michael Edic, Albany, NY (US); Samit Basu, Niskayuna, NY (US); Nadeem Ishaque, Clifton Park, NY (US); Deborah Walter, Burnt Hills, NY (US); John McLeod, Alplaus, NY (US)

(73) Assignee: General Electric Company, Niskayuna, NY (US)

( * ) Notice: Subject to any disclaimer, the term of this patent is extended or adjusted under 35 U.S.C. 154(b) by 425 days.

(21) Appl. No.: 10/334,302

(22) Filed: Dec. 31, 2002

(65) Prior Publication Data

US 2004/0125917 A1 Jul. 1, 2004

(51) Int. Cl.
*A61B 6/00* (2006.01)
(52) U.S. Cl. .................................. 378/19; 250/370.09
(58) Field of Classification Search ................ 378/19; 250/370.09
See application file for complete search history.

(56) References Cited

U.S. PATENT DOCUMENTS

| | | | | |
|---|---|---|---|---|
| 5,164,973 A * | 11/1992 | Takahashi et al. | ............. | 378/19 |
| 5,303,282 A * | 4/1994 | Kwasnick et al. | ........... | 378/147 |
| 5,912,938 A * | 6/1999 | Dobbs et al. | ................ | 378/19 |
| 6,047,040 A * | 4/2000 | Hu et al. | ..................... | 378/19 |
| 6,479,824 B1 * | 11/2002 | Hoffman | ..................... | 250/367 |

* cited by examiner

*Primary Examiner*—Edward J. Glick
*Assistant Examiner*—Jurie Yun
(74) *Attorney, Agent, or Firm*—Fletcher Yoder

(57) ABSTRACT

A method and apparatus for providing a configurable field of view in a non-invasive imaging system, such as a CT medical imaging system. A detector structure comprising two or more flat-panel X-ray detectors is provided such that the configurable field of view may encompass the full area of the two or more X-ray detectors or any suitable subset of the full area. The field of view may be configured based upon an acceptable field of view in conjunction with an acceptable scan speed.

20 Claims, 4 Drawing Sheets

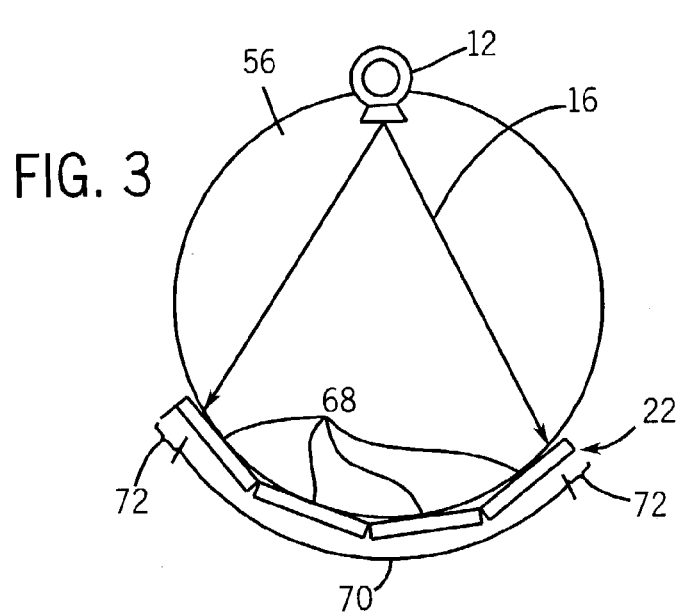
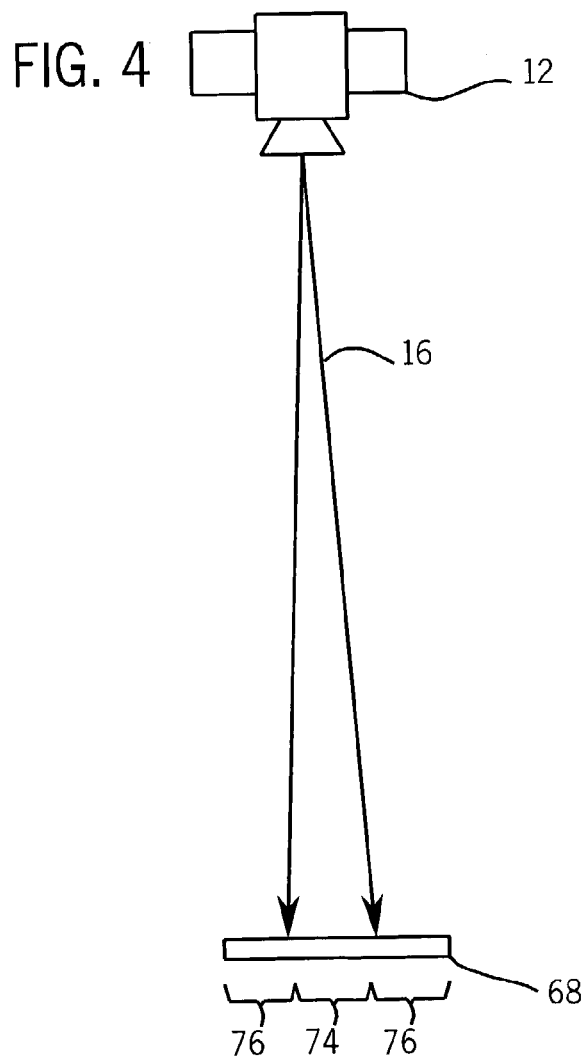

VOLUMETRIC CT SYSTEM AND METHOD UTILIZING MULTIPLE DETECTOR PANELS

BACKGROUND OF THE INVENTION

The present invention relates generally to the field of non-invasive imaging and, more specifically, to the field of medical imaging using Computed Tomography systems.

Computed Tomography (CT) imaging systems measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced projection images. It should be pointed out that a CT system produces data that represents the line integral of linear attenuation coefficients of the scanned object. This data is then reconstructed to produce an image which is typically displayed on a cathode ray tube, and may be printed or reproduced on film. A virtual 3-D image may also be produced by a CT examination.

CT scanners operate by projecting fan shaped or cone shaped X-ray beams from an X-ray source that is collimated and passes through the object, such as a patient, that is then detected by a set of detector elements. The detector element produces a signal based on the attenuation of the X-ray beams, and the data are processed to produce signals that represent the line integrals of the attenuation coefficients of the object along the ray paths. These signals are typically called projections. By using reconstruction techniques, such as filtered backprojection, useful images are formulated from the projections. The locations of pathologies may then be located either automatically, such as by a computer assisted diagnosis (CAD) algorithm or, more conventionally, by a trained radiologist.

However, CT detectors may not provide sufficient resolution to accurately resolve structures on the order of 0.5 to 1.5 mm, which may still be of diagnostic and pathological interest. This lack of resolution may be problematic in applications where greater resolution is desired, such as inner ear imaging, cardiac and vascular imaging, small animal imaging, and oncological screening.

In addition, it is often desirable to image large volumes inside the body while maintaining a desired X-ray dosage. For example, in cardiac CT imaging it is generally desirable to capture the entirety of the heart in one rotation of the scanner. Likewise, in whole-organ perfusion assessment it is generally desirable to capture the entire organ within a single rotation. However, other CT imaging applications may not require as extensive a field of view and, indeed, there may be scanning speed benefits associated with a smaller field of view. Therefore, it may be advantageous to be able to vary the field of view, balancing the desired field of view with the desired scan speed. It may therefore be desirable to provide high resolution in conjunction with a configurable field of view.

BRIEF DESCRIPTION OF THE INVENTION

The present technique provides a means for increasing the available field of view of an imaging system while also increasing the available resolution of the imaging system. In particular, an imaging system is provided in which the detector comprises two or more flat-panel X-ray detectors arranged generally adjacent to one another. The field of view encompassed by the two or more flat panels is configurable such that the field of view, the scan time, and the scan resolution may be optimized in accordance with the scanning application.

In accordance with one embodiment of the present technique, a method is provided for non-invasively acquiring an image representative of the internal features of a target. An X-ray beam is emitted from an X-ray source such that at least a portion of the X-ray beam passes through a target. The portion of the X-ray beam is detected on a detector. The detector comprises two or more flat-panel X-ray detectors which generate two or more signals responsive to the portion of the X-ray beam within an arbitrary field of view. The arbitrary field of view is defined within an area encompassed by the two or more flat-panel X-ray detectors. The two or more signals within the arbitrary field of view are acquired and processed to reconstruct an image representative of the internal features of the target.

In accordance with another aspect of the present technique, a tangible medium for generating an image representative of the internal features of a target is provided. The tangible medium includes a routine for acquiring two or more signals within an arbitrary field of view defined within an area encompassed by two or more flat-panel X-ray detectors. In addition, the tangible medium includes a routine for processing the two or more signals from the arbitrary field of view to reconstruct an image representative of the internal features of a target.

In accordance with an additional aspect of the present technique, an imaging system is provided. The imaging system includes an X-ray source configured to emit a beam of X-rays toward an imaging target and a detector configured to detect the beam of X-rays and to generate two or more signals in response to the beam of X-rays. The detector comprises two or more flat-panel X-ray detectors which encompass a configurable field of view. The imaging system also includes an X-ray controller configured to control the X-ray source and data acquisition circuitry configured to receive the two or more signals from the detector. In addition, the system includes a computer configured to receive the two or more signals from at least one of the data acquisition circuitry and memory circuitry and to reconstruct an image representative of the internal features of the imaging target. An operator workstation configured to transmit one or more commands to at least one of the computer, the data acquisition circuitry, and the X-ray controller is also included.

In accordance with another aspect of the present technique, an imaging system is provided. The imaging system includes an X-ray source configured to emit a beam of X-rays toward an imaging target and a detector configured to detect the beam of X-rays and to generate two or more signals in response to the beam of X-rays. The detector comprises two or more flat-panel X-ray detectors. The imaging system also includes an X-ray controller configured to control the X-ray source and data acquisition circuitry configured to receive the two or more signals from the detector. In addition, the system includes a computer configured to receive the two or more signals from at least one of the data acquisition circuitry and memory circuitry and to reconstruct an image representative of the internal features of the imaging target. An operator workstation configured to transmit one or more commands to at least one of the computer, the data acquisition circuitry, and the X-ray controller is also included. The system also includes means for configuring an arbitrary field of view encompassed by the two or more flat-panel X-ray detectors.

BRIEF DESCRIPTION OF THE DRAWINGS

The foregoing and other advantages and features of the invention will become apparent upon reading the following detailed description and upon reference to the drawings in which:

FIG. 3 is a diagrammatical view of the detector configuration of FIGS. 1 and 2 as seen down the aperture of the gantry;

FIG. 4 is a diagrammatical view of the detector configuration of FIGS. 1 and 2 as seen from the side of the aperture.

DETAILED DESCRIPTION OF SPECIFIC EMBODIMENTS

Figure 1:
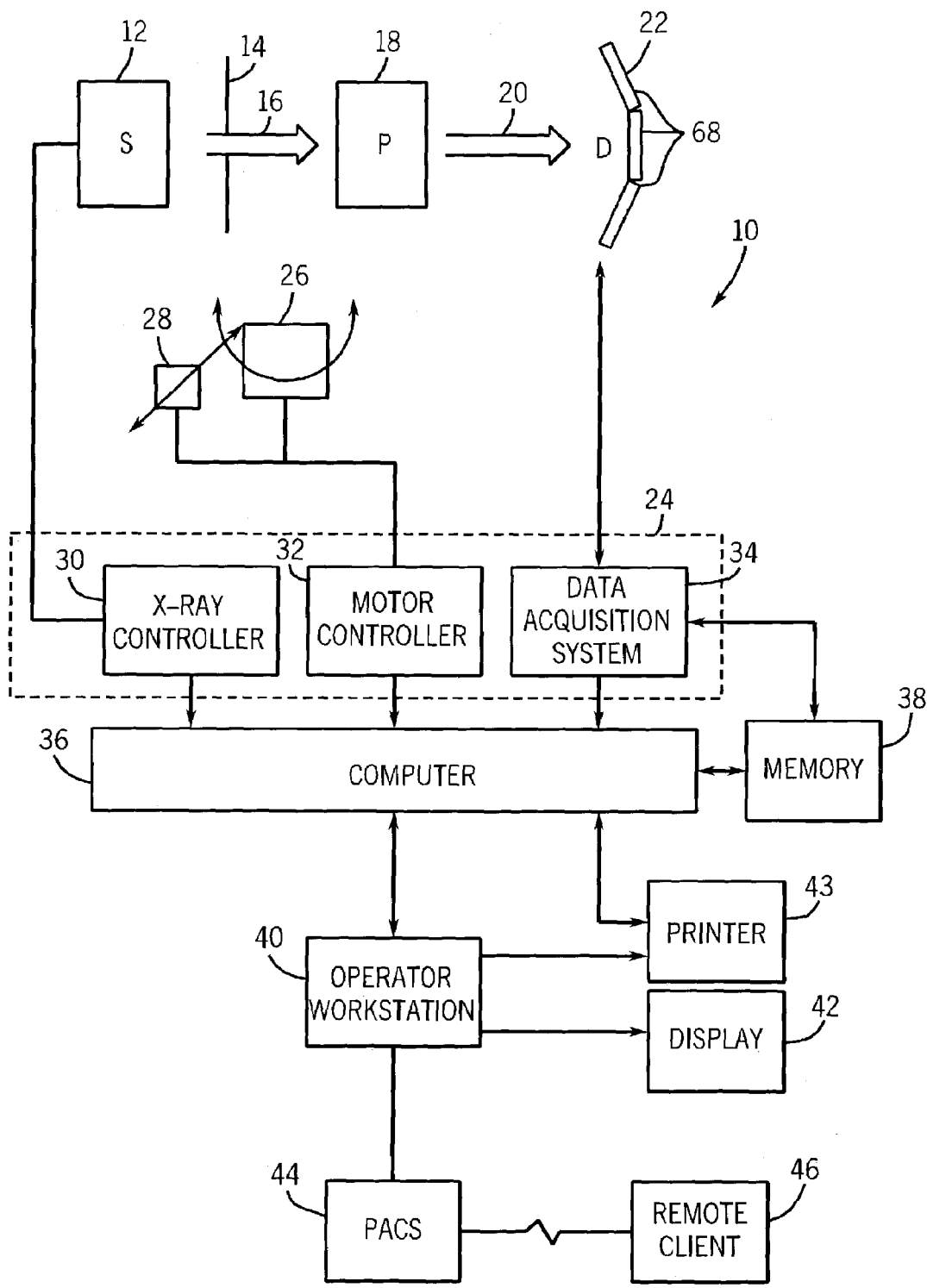
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the illustrated embodiment, system 10 is a computed tomography (CT) system designed both to acquire original image data, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube. Collimator 14 permits a stream of radiation 16 to pass into a region in which a subject, such as a human patient 18 is positioned.

A portion of the radiation 20 passes through or around the subject and impacts a detector, represented generally at reference numeral 22. Elements of the detector 22 produce electrical signals that represent the intensity of the incident X-ray beam. These signals are acquired and processed to reconstruct an image of the features within the subject.

Source 12 is controlled by a system controller 24 which furnishes both power and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a rotational subsystem 26 and linear positioning subsystem 28. The rotational subsystem 26 enables the X-ray source 12, collimator 14 and the detector 22 to be rotated one or multiple turns around the patient 18. It should be noted that the rotational subsystem 26 may include a gantry. Thus, the system controller 24 may be utilized to operate the gantry. The linear positioning subsystem 28 enables the patient 18, or more specifically a patient table or platform, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 within the system controller 24. Particularly, the X-ray controller 30 is configured to provide power and timing signals to the X-ray source 12. A motor controller 32 may be utilized to control the movement of the rotational subsystem 26 and the linear positioning subsystem 28.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 and moreover, to a memory 38. It should be understood that any type of memory to store a large amount of data may be utilized by such an exemplary system 10. Also the computer 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image and to control imaging. Additionally, the scanned image may also be printed on to a printer 43 which may be coupled to the computer 36 and the operator workstation 40. Further, the operator workstation 40 may also be coupled to a picture archiving and communications system (PACS) 44. It should be noted that PACS 44 may be coupled to a remote system 46, radiology department information system (RIS), hospital information system (HIS) or to an internal or external network, so that others at different locations may gain access to the image and to the image data.

It should be further noted that the computer 36 and operator workstation 40 may be coupled to other output devices which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
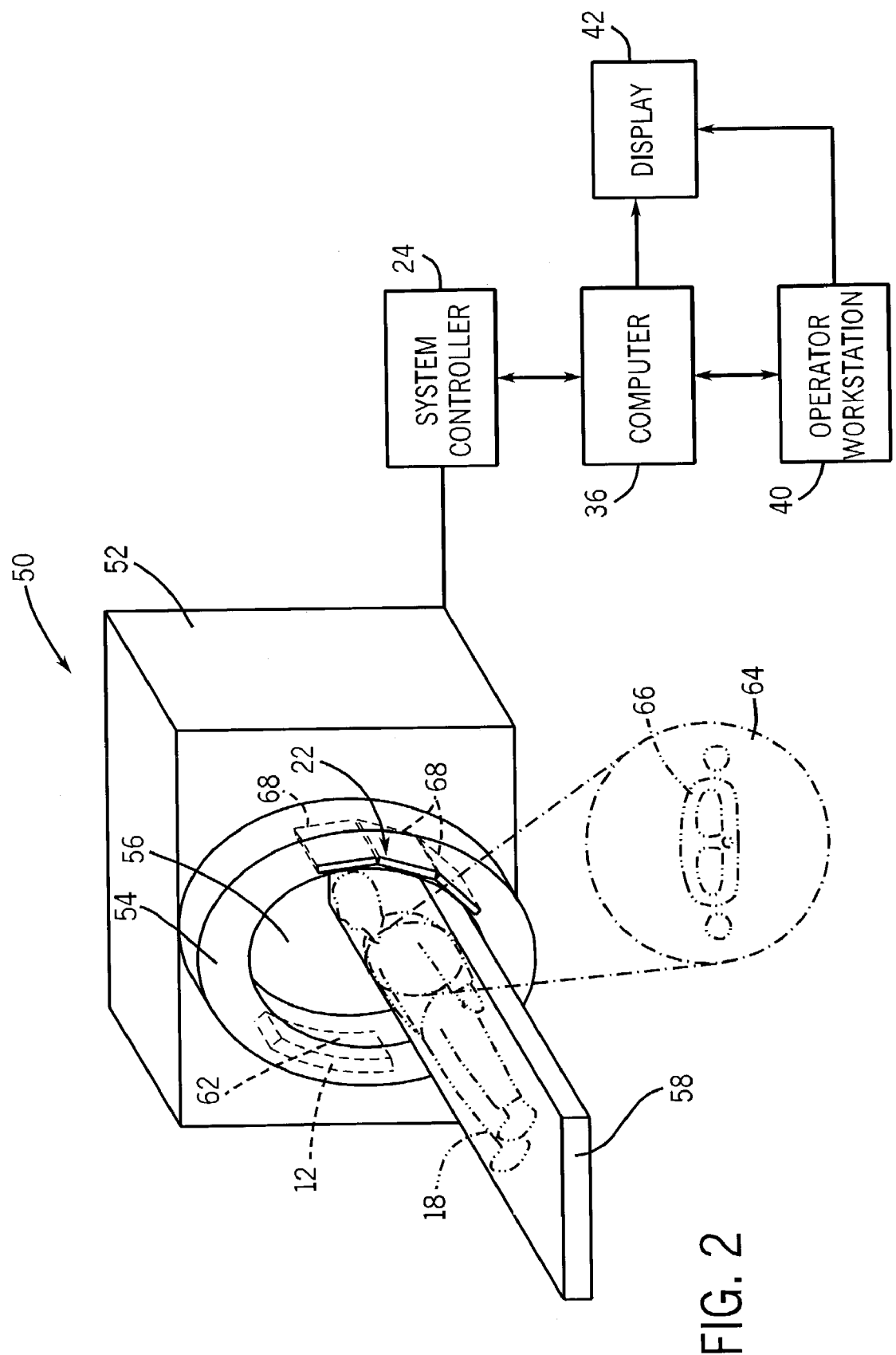
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is illustrated with a frame 52 and a gantry 54 that has an aperture 56. The aperture 56 may typically be 50 cm in diameter. Further, a patient table 58 is illustrated positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 28 (see FIG. 1). The gantry 54 is illustrated with the source of radiation 12, typically an X-ray tube which emits X-ray radiation from a focal point 62. The stream of radiation is directed towards a particular region of the patient 18. It should be noted that the particular region of the patient 18 is typically chosen by an operator so that the most useful scan of a region may be imaged.

In typical operation, X-ray source 12 projects an X-ray beam from the focal point 62 and toward detector 22. The detector 22 is generally formed by a plurality of detector elements which sense the X-rays that pass through and around a subject of interest, such as particular body parts, for instance the liver, pancreas and so on. Each detector element produces an electrical signal that represents the intensity of the X-ray beam at the position of the element at the time the beam strikes the detector.

Furthermore, the gantry 54 is rotated around the subject of interest so that a plurality of radiographic views may be collected by the computer 36. Thus, an image or slice is acquired which may incorporate, in certain modes, less or more than 360 degrees of projection data, to formulate an image. The image is collimated to a desired thickness, typically less than 40 mm using either lead shutters in front of the X-ray source 12 and different detector apertures 22. The collimator 14 (see FIG. 1) typically defines the size and shape of the X-ray beam that emerges from the X-ray source 12.

Thus, as the X-ray source 12 and the detector 22 rotate, the detector 22 collects data of the attenuated X-ray beams. Data collected from the detector 22 then undergoes pre-processing and calibration to condition the data to represent the line integrals of the attenuation coefficients of the scanned objects. The processed data, commonly called projections, are then filtered and backprojected to formulate an image of the scanned area. As mentioned above, the computer 36 is typically used to control the entire CT system 10. The main computer that controls the operation of the system may be adapted to control features enabled by the system controller 24. Further, the operator workstation 40 is coupled to the computer 36 as well as to a display, so that the reconstructed image may be viewed.

Once reconstructed, the image produced by the system of FIGS. 1 and 2 reveals internal features of a patient. As illustrated generally in FIG. 2, the image 64 may be displayed to show these features, such as indicated at reference numeral 66 in FIG. 2. In traditional approaches to diagnosis of medical conditions, such as disease states, and more generally of medical events, a radiologist or physician would consider a hard copy of display of the image 64 to discern characteristic features of interest. Such features might include lesions, sizes and shapes of particular anatomies or organs, and other features which would be discernable in the image based upon the skill and knowledge of the individual practitioner. Other analyses may be based upon capabilities of various CAD algorithms. Subsequent processing and data acquisition is, then, entirely at the discretion and based upon the expertise of the practitioner.

The diagnostic value of the reconstructed image 64, however, may be limited for various reasons. For example, the X-ray detectors employed in CT scanners are typically configured as a linear array composed of one or more rows of detector elements. For instance, four or eight rows of detector elements may be present in multislice CT scanners while a single row is present in a single slice CT scanner. The limited number of rows of detector elements, even in multislice systems, provide a coverage along the patient axis, i.e., z-coverage, which may not be satisfactory for certain CT image applications at a desired X-ray dosage. For example, cardiac and whole-organ perfusion imaging may benefit from a larger coverage along the patient axis that would allow the acquisition of image data for the entire organ within a single rotation.

In addition, each row may contain about 1,000 detector elements, often referred to as pixels, which have a pixel pitch of approximately 1 mm. This pixel pitch provides sufficient resolution to detect anatomical features on the order of 1–2 mm in diameter after post-processing of the acquired image data. However certain imaging applications, such as inner ear imaging, cardiac and vascular imaging, small animal imaging, and oncological screening, may benefit from greater CT image resolution. In particular, these types of applications may be improved by being able to reliably resolve structures with dimensions smaller than the 1–2 mm noted above.

One approach that may be used to increase the available field of view, both in the scanning plane and along the patient axis, and the image resolution is to form the detector 22 from two or more flat-panel X-ray detectors 68, as depicted in FIGS. 1 and 2. The flat-panels 68 possess high isotropic resolution as well as a large field of view. The flat-panels 68 may be based upon the amorphous silicon technology found in digital X-ray imaging systems used in medical imaging. These flat-panels 68 may consist of large, monolithic arrays of photolithographically created high-density photodiodes coupled to a continuous X-ray scintillator. When the scintillator is struck by X-ray radiation, such as X-ray beam 16 or 20, it generates visible light that may be detected by the photodiodes. The photodiodes are in turn connected to data acquisition circuitry which measures and records these signals. The photodiode pitch may be about 200 microns, providing resolution of structures between 0.2–0.4 mm in diameter after post-processing of the acquired image data.

The panels 68 may be situated generally adjacent to one another and tangential to the circular arc of the gantry. By tiling flat-panel detectors 68 together, a field of view large enough to accommodate the clinical scanning of humans or large animals may be created. While the flat-panel detectors 68 are depicted in FIG. 2 as being arranged generally linearly, the panels 68 may also be arranged in a staggered manner, i.e., such that the edges are not precisely aligned, or in other manners which may be suitable for various scanning techniques, such as helical scans.

The increased field of view along the patient axis provided by the use of tiled flat-panels 68, however, may not be desired for many applications. In applications where the increased filed of view is not desired, the increased scan time associated with the larger field of view may also not be desired. For instance, in an embodiment where the detector 22 comprises two 20 cm digital flat panels 68 with a native frame rate of 30 Hz, 900 full-panel projection views may be acquired in approximately 30 seconds. However, if the data readout is limited to the central 360 rows of the panel, 1,000 partial panel views may be obtained in approximately 8 seconds.

Therefore it may be desirable to provide an arbitrary field of view which may be configured by an operator such that the volume encompassed by the field of view and the scan time are optimized based upon the imaging application. The arbitrary field of view may be determined by configuring either or both of the in-plane field of view, determined by the number of detector panels employed in the system, or the field of view along the patient axis, i.e., the z-coverage, determined by the number of rows read out from each panel. Altering either of these parameters will affect the amount of data read out by the system.

Figure 5:
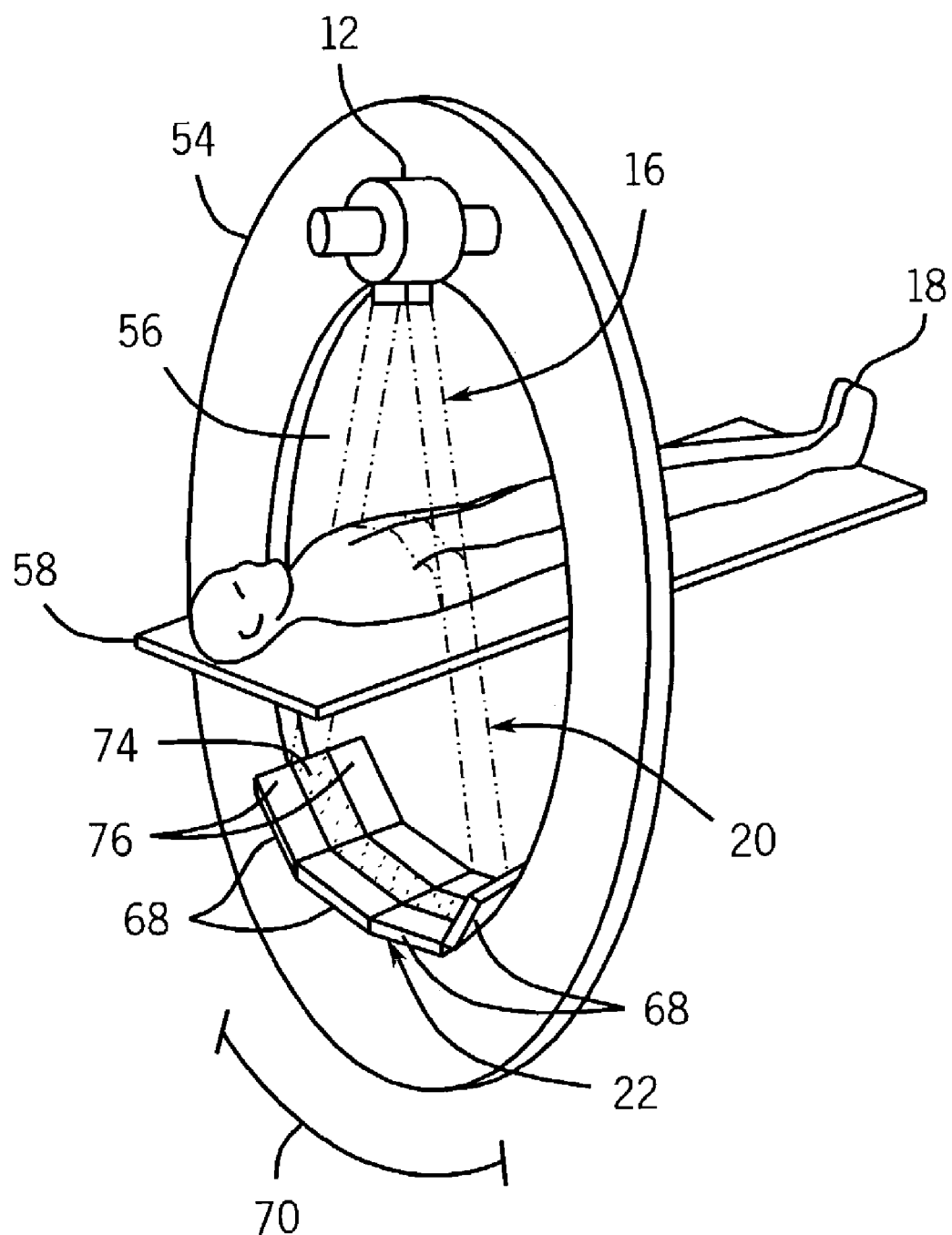
FIG. 5 is a diagrammatical view of the detector configuration of FIGS. 1 and 2 as seen from a three-dimensional perspective.

For example, referring to FIG. 3, the flat-panels 68 may largely encompass one dimension, defined by the arc 70, which determines the in-plane field-of-view, with only end-portions 72 of the detector 22 being outside the region read out by the acquisition circuitry 34. However, as depicted in FIG. 4, along a second dimension, the field of view along the patient axis read out by the data acquisition circuitry 34 may be reduced, thereby reducing the total image data acquired and allowing image acquisition to occur more rapidly. In FIG. 4 this is depicted as restricting data acquisition to the central region 74 of a flat panel 68, leaving end regions 76 unread, i.e., restricting z-coverage. A three-dimensional representation of an arbitrary field of view generally in accordance with the configuration depicted in FIGS. 3 and 4 is provided by FIG. 5.

Other options are of course possible, depending on the desired field of view and scan speed. For example, the field of view dimension represented in FIG. 3 as arc 70 may instead be reduced or the extent of region 74 read in the dimension represented in FIG. 4 may be increased or decreased to adjust the imaged volume and the associated scan time. Likewise, it is not necessary that each panel 68 comprising the detector 22 be read out identically, but instead the area of each panel 68 which is read out may vary to accommodate various scanning techniques, such as helical scan acquisitions.

Likewise, within panels 68, readout may be accomplished by binning two or more adjacent rows or columns to decrease data acquisition time at the expense of image resolution. In this embodiment, image resolution, not image volume, may be sacrificed to reduce scan time. Similarly, photodiodes within the flat-panels 68 may be selectively read out to create a custom or arbitrary field of view within the area encompassed by the flat panels 68, as determined by the operator and the application.

While the invention may be susceptible to various modifications and alternative forms, specific embodiments have been shown by way of example in the drawings and have been described in detail herein. However, it should be understood that the invention is not intended to be limited to the particular forms disclosed. Indeed, the techniques discussed herein may be applicable to non-medical imaging applications, such as is package and baggage screening and other forms of security and non-invasive screening where the interior of an imaged object is to be visualized. Rather, the invention is to cover all modifications, equivalents, and alternatives falling within the spirit and scope of the invention as defined by the following appended claims.

What is claimed is:

1. A method for non-invasively acquiring an image representative of the internal features of a target, comprising:
   emitting an X-ray beam from an X-ray source such that at least a portion of the X-ray beam passes through a target;
   detecting at least the portion of the X-ray beam on a detector comprising two or more flat-panel X-ray detectors which generate two or more signals responsive to the portion of the X-ray beam within an arbitrary field of view, wherein the arbitrary field of view is defined within an area encompassed by the two or more flat-panel X-ray detectors;
   acquiring the two or more signals within the arbitrary field of view; and
   processing the two or more signals from the arbitrary field of view to reconstruct an image representative of the internal features of the target.

2. The method as recited in claim 1, wherein acquiring the two or more signals within the arbitrary field of view comprises acquiring two or more signals detected by a central region across the two or more flat panel X-ray detectors.

3. The method as recited in claim 1, wherein acquiring the two or more signals within the arbitrary field of view comprises selectively reading out two or more rows of photodiodes of the two or more flat-panel X-ray detectors, wherein the photodiodes to be read out are selected by at least one of an operator and a computer algorithm.

4. The method as recited in claim 3, wherein the photodiodes to be read out are selected such that the arbitrary field of view and a scan time are optimized for an imaging application.

5. The method as recited in claim 3, wherein the photodiodes to be read out are selected such that the arbitrary field of view, a scan time, and an image resolution are optimized for an imaging application.

6. A computer-readable medium for generating an image representative of the internal features of a target, comprising:
   a routine for acquiring two or more signals within an arbitrary field of view defined within an area encompassed by two or more flat-panel X-ray detectors; and
   a routine for processing the two or more signals from the arbitrary field of view to reconstruct an image representative of the internal features of a target.

7. The computer-readable medium as recited in claim 6, wherein the routine for acquiring the two or more signals within the arbitrary field of view acquires two or more signals detected by a central region across the two or more flat panel X-ray detectors.

8. The computer-readable medium as recited in claim 6, wherein the routine for acquiring the two or more signals within the arbitrary field of view selectively reads out two or more photodiodes of the two or more flat-panel X-ray detectors.

9. The computer-readable medium as recited in claim 8, wherein the photodiodes to be read out are selected such that the arbitrary field of view and a scan time are optimized for an imaging application.

10. The computer-readable medium as recited in claim 8, wherein the photodiodes to be read out are selected such that the arbitrary field of view, a scan time, and an image resolution are optimized for an imaging application.

11. An imaging system capable of generating images representative of the internal features of an imaging target, comprising:
   an X-ray source configured to emit a beam of X-rays toward an imaging target;
   a detector configured to detect the beam of X-rays and to generate two or more signals in response to the beam of X-rays, wherein the detector comprises two or more flat-panel X-ray detectors which encompass a configurable field of view;
   an X-ray controller configured to control the X-ray source;
   data acquisition circuitry configured to receive the two or more signals from the detector;
   a computer configured to receive the two or more signals from at least one of the data acquisition circuitry and memory circuitry and to reconstruct an image representative of the internal features of the imaging target; and an operator workstation configured to transmit one or more commands to at least one of the computer, the data acquisition circuitry, and the X-ray controller.

12. The imaging system as recited in claim 11, further comprising:

a gantry incorporating the X-ray source and the detector;
a platform configured to be positioned within the gantry;
a rotational subsystem configured to rotate the gantry; and
a linear positioning subsystem configured to position the platform within the gantry.

13. The imaging system as recited in claim 11, wherein the configurable field of view is sized in accordance with one or more parameters received from at least one of the computer or the operator workstation.

14. The imaging system as recited in claim 11, wherein the configurable field of view is configured based upon a desired field of view and a desired scan time.

15. The imaging system as recited in claim 14, wherein one or more acquisition commands received from at least one of the operator workstation or the computer establish the desired field of view.

16. The imaging system as recited in claim 11, wherein the configurable field of view is configured based upon a desired field of view, a desired scan time, and a desired image resolution.

17. The imaging system as recited in claim 16, wherein one or more acquisition commands received from at least one of the operator workstation or the computer establish the desired field of view.

18. The imaging system as recited in claim 11, wherein the imaging system is a CT imaging system.

19. An imaging system capable of generating images representative of the internal features of an imaging target, comprising:

an X-ray source configured to emit a beam of X-rays toward an imaging target;
a detector configured to detect the X-ray beams and to generate two or more signals in response to the beam of X-rays, wherein the detector comprises two or more flat-panel X-ray detectors;
an X-ray controller configured to control the X-ray source;
data acquisition circuitry configured to receive the two or more signals from the detector;
a computer configured to receive the two or more signals from at least one of the data acquisition circuitry and memory circuitry and to reconstruct an image representative of the internal features of the imaging target; and
an operator workstation configured to transmit one or more commands from an operator to at least one of the computer, the data acquisition circuitry, and the X-ray controller; and
means for configuring an arbitrary field of view encompassed by the two or more flat-panel X-ray detectors.

20. The imaging system as recited in claim 19, further comprising:

a gantry incorporating the X-ray source and the detector;
a platform configured to be positioned within the gantry;
a rotational subsystem configured to rotate the gantry; and
a linear positioning subsystem configured to position the platform within the gantry.

* * * * *